United States Patent
Teles et al.

[11] Patent Number: 6,087,538
[45] Date of Patent: Jul. 11, 2000

[54] ADDITION REACTION OF HYDROXYL-CONTAINING COMPOUNDS WITH ALKYNES OR ALLENES

[75] Inventors: Joaquim Henrique Teles, Altrip; Norbert Rieber, Mannheim; Klaus Breuer, Altrip; Christopher William Rieker, Hassloch; Dirk Demuth, Mannheim; Hartmut Hibst, Schriesheim; Alfred Hagemeyer, Rheine, all of Germany

[73] Assignee: BASF Aktiengesellschaft, Ludwigshafen, Germany

[21] Appl. No.: 09/092,059

[22] Filed: Jun. 5, 1998

[30] Foreign Application Priority Data

Jun. 23, 1997 [DE] Germany ............... 197 26 666

[51] Int. Cl.⁷ ............... C07C 43/30; C07C 2/02; B01J 21/08
[52] U.S. Cl. ............... 568/591; 502/250; 585/530
[58] Field of Search ............... 568/591; 585/530; 502/250

[56] References Cited

U.S. PATENT DOCUMENTS 4,371,730  2/1983  Eastman ............... 585/333

FOREIGN PATENT DOCUMENTS 239 752  3/1946  Switzerland .

OTHER PUBLICATIONS

Database WPI, Derwent Publications, AN 76–18332x, SU 449 034, Jul. 18, 1975.

Chemical Abstracts, vol. 112. No. 7, Feb. 12, 1990, AN 54986a, DD 267 629, May 10, 1989.

Chemical Abstracts, vol. 112, No. 7, Feb. 12, 1990, AN 54987b, DD 265 289, Mar. 01, 1989.

*Primary Examiner*—Elli Peselev
*Attorney, Agent, or Firm*—Oblon, Spivak, McClelland, Maier & Neustadt, P.C.

[57] ABSTRACT

Compounds of the formula I and II

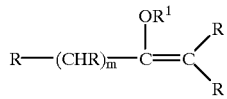

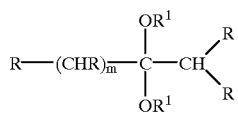

where $R^1$ is hydrogen or an aliphatic, cycloaliphatic, araliphatic, aromatic or heterocyclic radical or an acyl radical, it being possible for these radicals to carry further substituents which do not react with acetylenes or allenes, and the radicals R, independently of one another, are hydrogen or aliphatic, cycloaliphatic, araliphatic, aromatic or heterocyclic radicals which may be linked to one another with formation of a ring and m is 0 or 1, are prepared by an addition reaction of a compound of the formula III $$R^1OH \qquad III$$

with an acetylene or allene of the formula IV or V

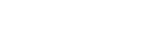

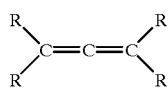

where $R^1$ and R have the abovementioned meanings, in the gas phase at elevated temperatures in the presence of a heterogeneous, silicate-containing catalyst, by a process in which the catalyst used contains, as an active component, an X-ray amorphous zinc silicate or cadmium silicate containing from 1 to 40% by weight, calculated as oxide, of zinc or cadmium and is obtainable by applying a zinc salt or cadmium salt of an organic acidic compound which is decomposable at below 400° C., to an amorphous silica and forming the catalyst at from 50 to 500° C., in the presence of a hydroxyl-containing compound selected from the group consisting of water, alkanols with up to 10 carbon atoms, diols and polyols having 2 to 6 carbon atoms and 2 or 3 OH groups and carboxylic acids of 1 to 6 carbon atoms.

12 Claims, 1 Drawing Sheet

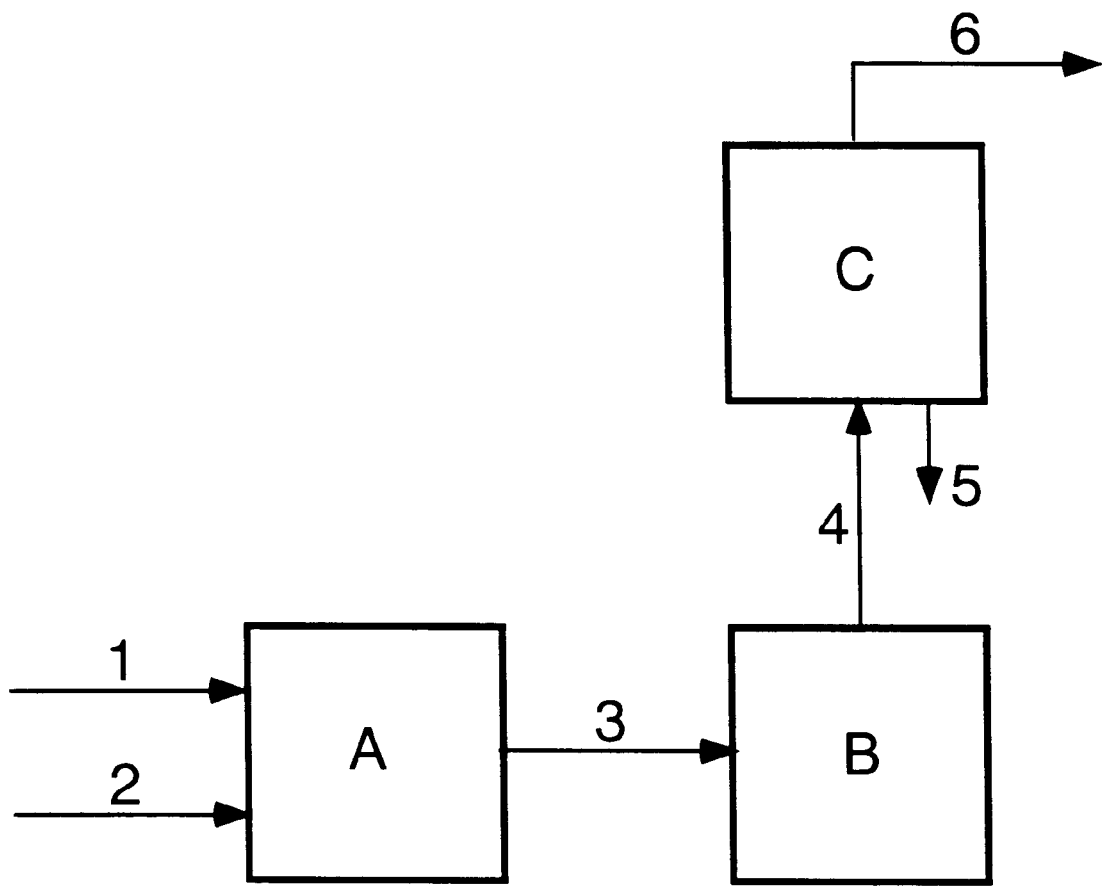

ADDITION REACTION OF HYDROXYL-CONTAINING COMPOUNDS WITH ALKYNES OR ALLENES

The present invention relates to a process for the addition reaction of hydroxyl-containing compounds with alkynes or allenes with formation of aldehydes and ketones or derivatives thereof in the form of enol ethers or acetals or ketals in the presence of an amorphous zinc silicate or cadmium silicate catalyst. The present invention furthermore relates to a novel process for the preparation of zinc silicate or cadmium silicate and to the catalyst thus obtained.

The addition reaction of hydroxyl-containing compounds with alkynes or allenes is carried out almost exclusively using homogeneously dissolved catalysts, for example with acids, bases and transition metal complexes (cf. Houben-Weyl, Methoden der organischen Chemie, Vol. 6/3, page 233, page 90, Vol. 5/2a, page 20 738, Vol. 6/1d, page 136 and Vol. 7/a, page 816).

The acid catalysis is generally limited to the addition reaction with activated, electron-rich alkynes (such as acetylene ethers, R—C≡—C—OR', acetylene thioethers, R—C≡—C—SR' and acetyleneamines, R—C≡—C—NR'$_2$).

Under base catalysis (in the presence of KOH or alcoholate), alcohols can also be subjected to an addition reaction with unactivated alkynes in the liquid phase. This is the most commonly used method; however, reaction requires high temperatures and pressures and the space-time yield is relatively low. Typically, residence time from 6 to 10 hours at about 160° C. and from 18 to 20 bar pressure is required for the base-catalyzed vinylation of an alcohol.

The addition reaction can also be catalyzed by transition metal complexes in the liquid phase. Mercury(II) or gold(1) salts are particularly suitable for the addition reaction of alcohols, while zinc salts and cadmium salts are preferred for the addition reaction of carboxylic acids and phenols.

The addition reaction of carboxylic acids (in particular acetic acid and propionic acid), with acetylene can also be carried out in the gas phase in the presence of appropriate zinc carboxylates (including basic zinc carboxylates according to CH 239 752) on carriers having a large surface area as catalysts.

Finally, the addition reaction of methanol with propyne or propadiene in the gas phase in the presence of zinc oxide on active carbonate or silica gel has also been described in DD 265 289, and that in the presence of zinc nitrate on active carbon or silica gel in DD 267 629.

All these prior processes have disadvantages. They either have only a limited field of use or, like the base-catalyzed addition reaction, require high pressures and temperatures, which may lead to safety problems, or they have only a low space-time yield. Homogeneously dissolved transition metal catalysts are often deactivated after a small number of cycles and are furthermore difficult to recycle. Heterogeneous catalysts for the addition reaction with alkynes or allenes have been described only rarely to date. Zinc carboxylates or cadmium carboxylates on active carbon catalyze only the addition reaction of carboxylic acids (e.g. acetic acid or propionic acid) with acetylene. The abovementioned catalysts based on zinc oxide on active carbon or silica gel (DD 265 289) is capable of catalyzing the addition reaction of alcohols (methanol or ethanol) with propyne or propadiene with good selectivity (from 90 to 96%), but the catalytic activity is relatively low and the required reaction temperatures are high and the required contact times are long. At the same temperature, zinc nitrate on active carbon or silica gel is about an order of magnitude less active than zinc oxide and the selectivity is much lower (max. 70%).

It is an object of the present invention to provide a heterogeneous catalyst for the addition reaction of hydroxyl-containing compounds with alkynes, allenes or mixtures thereof, which catalyst is very active and selective at low temperatures.

We have found that this object is achieved, according to the invention, by a process for the preparation of compounds of the formulae I and II

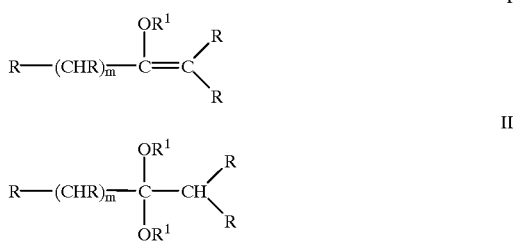

where R$^1$ is hydrogen or an aliphatic, cylcoaliphatic, araliphatic, aromatic or heterocyclic radical or an acyl radical, it being possible for these radicals to carry further substituents which do not react with acetylenes or allenes, radicals R, independently of one another, are hydrogen or aliphatic, cycloaliphatic, araliphatic, aromatic or heterocyclic radicals which may be bonded to one another with formation of a ring, and m is 0 or 1, by addition reaction of a compound of the formula III $$R^1OH \qquad\qquad III$$

with an acetylene or allene of the formula IV or V

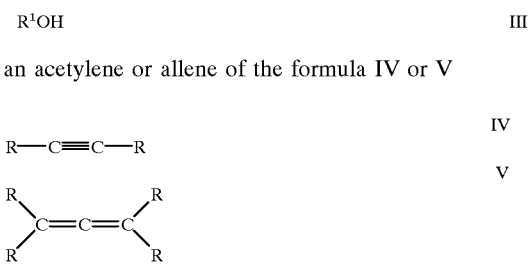

where R$^1$ and R have the abovementioned meanings, in the gas phase at elevated temperatures in the presence of a heterogeneous, silicate-containing catalyst, wherein the catalyst used contains, as an active component, an X-ray amorphous zinc silicate or cadmium silicate containing from 1 to 40% by weight, calculated as oxide, of zinc or cadmium and having, for example, a BET surface area of from 10 to 1000 m$^2$/g and is obtainable by applying a zinc salt or cadmium salt of an organic acidic compound which is decomposable at below 400° C., preferably a formate, acetylacetonate or acetate, to amorphous silica and forming the catalyst at from 50 to 500° C., in the presence of a hydroxyl-containing compound selected from the group consisting of water, alkanols of 1 to 10 carbon atoms, diols or polyols having 2 to 6 carbon atoms and 2 or 3 OH groups and carboxylic acids of 1 to 6 carbon atoms.

BRIEF DESCRIPTION OF THE DRAWINGS

FIG. 1 is a block diagram of the process of the invention.

The alkanol for forming the catalyst is advantageously the same alkanol R$^1$OH, which is subjected to the addition reaction with the acetylene or allene. The catalyst to be used according to the invention may be doped with up to 80, preferably up to 50, in particular up to 20, mol per cent of further metals selected from the group (A) consisting of sodium, potassium, lithium, cesium, beryllium, magnesium, calcium, strontium, barium, manganese, iron, cobalt, nickel and copper, and from the group (B) consisting of titanium, zirconium, hafnium, germanium, tin and lead.

In a preferred embodiment of the process, amorphous zinc silicate is used and 2-methoxypropene is prepared by the addition reaction of methanol with propyne and/or allene.

Suitable starting materials for the novel reaction are any desired alkynes or allenes or mixtures thereof. As a rule, however, technically readily obtainable acetylenes and allenes of 2 to 8 carbon atoms and of 3 to 8 carbon atoms, respectively, are used.

The hydroxyl-containing compound $R^1OH$ may be water, any desired alcohol, a phenol or a carboxylic acid. In general alcohols, in particular alkanols of 1 to 16 carbon atoms, mononuclear phenols and low molecular weight carboxylic acids, for example of 1 to 16 carbon atoms, are especially suitable.

The addition reaction of the hydroxyl-containing compounds is carried out in the presence of the heterogeneous catalyst in the gas phase, either over a fixed bed or in a fluidized bed, at from 50 to 400° C., preferably from 100 to 250° C., particularly preferably from 120 to 200° C., and from 0.1 to 100 bar, in particular from 0.5 to 20 bar (all pressures are based on the sum of the partial pressures of the starting materials).

For operational safety and for better heat removal, the reaction mixture can, if required, be diluted with inert gases, such as nitrogen, argon, low molecular weight alkanes or olefins.

The molar ratio of hydroxyl-containing component to alkyne or allene may be from 0.01 to 100, preferably from 0.1 to 5, particularly preferably from 0.7 to 1.3

The selectivity of the reaction with respect to the mono- and diadducts can be controlled by means of the reaction conditions. Low ratios of hydroxyl-containing component to alkyne or allene and high temperatures and low partial pressures of the reactants lead to preferential formation of monoadducts, while high ratios of hydroxyl-containing component to alkyne or allene and low temperatures and high partial pressures of the reactants promote the formation of the bisadducts. For example, depending on the reaction conditions, 2-methoxypropene or 2,2-dimethoxypropane can be selectively formed from propyne or allene with methanol:

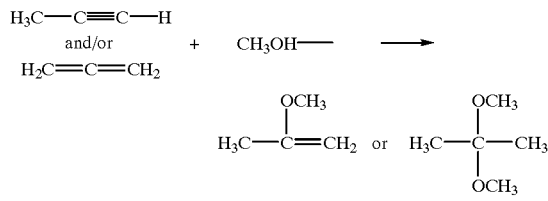

For the preparation of the catalyst, the amorphous $SiO_2$ carrier is advantageously impregnated with a solution of the zinc or cadmium salts of an organic acidic compound which are decomposable at below 400° C. Mixing the dry salts or the salts suspended in the alcohols $R^1OH$ with the carrier is possible but in general less advantageous.

The $SiO_2$ carrier is at least substantially amorphous, generally has a BET surface area of from 10 to 1000, preferably from 100 to 500, m²/g, and a water absorptivity of from 0.1 to 2, preferably from 0.7 to 1.3, ml/g and can be used in the form of a powder or of a prepared molding. The carrier can also be calcined prior to impregnation. Preferably, however, the carrier is not calcined.

Among the abovementioned salts, the zinc salts are preferred to the cadmium salts. Among the zinc salts, the zinc(II) salts, such as zinc formate, zinc acetylacetonate and in particular zinc acetate, which are soluble in lower alcohols and/or in water, are particularly suitable.

Ammoniacal zinc(II) acetate solution is particularly preferably used for the impregnations. These are carried out by catalyst preparation methods known per se. If required, for solubility reasons, the loading with zinc may also be effective in a plurality of successive impregnation steps.

If the carrier is used in the form of a powder, it can be brought into the desired shape prior to forming by shaping (for example by mixing, kneading and extrusion or pelleting).

To increase the pore volume, pore formers may also be added during the shaping (e.g. superabsorbers, such as Lutexal P® from BASF AG) or Walocel® (methylcellulose/synthetic resin combination from Wolff, Walsrode AG)).

Alternatively, another carrier, e.g. $Al_2O_3$, may furthermore be impregnated together with a silica precursor compound (e.g. $Si(OR)_4$) and with a zinc salt.

The zinc or cadmium loading may vary within wide limits, for example from 1 to 40% by weight, calculated as oxide. Zinc or cadmium contents of from 7 to 30, particularly preferably from 10 to 25, % by weight are preferred. The still inactive precatalyst thus obtained can then be calcined at not more than 600° C. in air or under inert gas. Calcination temperatures of from 80 to 300° C. are preferred. Calcination at from 120 to 250° C. in air is particularly preferred. In the calcination, it is advantageous to ensure that the temperature and residence time are chosen so that the molar ratio of the anion still present to zinc or cadmium does not fall below 0.1.

After the preparation of the precatalyst, forming, in which the actual active phase is formed preferably on the surface of the catalyst, is carried out prior to introduction into the reactor or in situ in the reactor. This gas/solid reaction is promoted at from 80 to 400° C. by the presence of water, alcohols, preferably lower alcohols, or carboxylic acids, preferably lower carboxylic acids. The catalyst is preferably formed at from 100 to 250° C. in a water- or methanol-containing gas mixture, particularly preferably at from 130 to 200° C. with a methanol-containing gas mixture in situ in the reactor in which the reaction with the alkyne or allene takes place. For the formation of the active phase, the precatalyst is advantageously brought into contact, under reaction conditions, with a mixture of methanol with propyne and allene and, if required, also other inert components, such as propene or propane. The formation of the active layer is indicated by the increase in the propyne and allene conversion (after from about 5 to 30 minutes, depending on the temperature), by the increase in the selectivity (after from 10 to 300 minutes, depending on the temperature) and by the decline in the concentration of methyl acetate in the exit gas when a precatalyst comprising zinc acetate is used. A steady state and high selectivity are achieved after from about 2 to 20 hours, depending on the temperature.

Standard methods are used for characterizing the catalyst samples (fresh samples as well as samples removed from the reactor). The measured BET surface area (as a rule from 10 to 800 m²/g) and the hardness are stated in the respective example. Catalysts having BET surface areas of from 100 to 400 m²/g are preferably used. Furthermore, the samples were thoroughly investigated by means of powder X-ray diffractometry (XRD) and transmission electron microscopy (TEM). Neither of the two structure analysis methods indicated any long-range order in the form of a crystalline structure, and all samples were amorphous. The distribution of the zinc over the carrier was investigated on sections under the electron microscope and using a microprobe. All samples including those removed from the reactor, showed that the catalyst has a substantially homogeneous elemental distribution and contains little or no crystalline ZnO. In the IR investigation (KBr pellet) the active catalyst showed no acetate bands (these are still visible in the precatalyst at 1570, 1410, 670 and 610 cm⁻¹). In the ¹³C-CP-MAS-NMR, too, acetate signals are no longer present. In the ²⁹Si-CP-MAS-NMR, the catalyst shows only the broad band at –109 ppm, typical of amorphous SiO₂, and a shoulder at –99 ppm (about 15% of the intensity of the main peak). The elemental analysis of a zinc acetate/SiO₂ precatalyst showed that the molar acetate/zinc ratio depends on the calcination temperature. Catalysts dried at room temperature have an acetate/zinc ratio of from 1.8 to 2. After the calcination in the preferred temperature range of from 200 to 250° C., the acetate/zinc ratio is from 0.5 to 1. At higher temperatures, the acetate/zinc ratio decreases even further as does the catalytic activity of the catalysts formed therefrom.

For the reaction, the catalyst may be arranged as a fixed bed or, for example, also used in a fluidized bed and may have an appropriate form for this purpose, such as chips, pellets, monoliths, beads or extrudates (extrudates having appropriate cross-sections, such as solid extrudate, a wagon wheel, a star or a ring).

(a) General Reaction Conditions

The catalytic reactions according to FIG. 1 were carried out in a gradient-free CSTR (Continuously Stirred Tank Reactor) (A) having a volume of 1740 ml and a catalyst volume of about 90 ml, modified for heterogeneous gasphase reactions. The reactor had an internal diameter of about 108 mm and a height of about 200 mm and was heated by means of an electrical heating coil mounted on the inner surface. A small metal cylinder (diameter about 64 mm, height about 150 mm) was mounted in the middle of the reactor and was provided at half height (about 85 mm below the upper edge) with a wire grid. The catalyst was poured loosely onto this wire grid. A flat turbine (diameter about 100 mm, height about 20 mm) which was driven at 1500–2000 rpm was present on the reactor cover. A total of 6 thermocouples for temperature monitoring were mounted at different heights along the reactor axis. The starting materials were metered under pressure by means of HPLC pumps, mixed shortly before the reactor and let down into the reactor space. The alkyne or allene (1 in FIG. 1) was metered in either in pure form or in dilute form as a mixture with other inert components. In the case of propyne and allene, a mixture with other hydrocarbons was used, (composition: 30–43% by volume of propyne, 16–20% by volume of allene, 20–45% by volume of propene, 5–10% by volume of isobutane and 2–6% by volume of propane as main components; all other components less than 1%. This mixture was obtained by distillation from a side stream of a steam cracker).

About 10% by weight of cyclohexane as an internal standard for the GC analysis were metered into the alcohol component (2 in FIG. 1).

The reaction was carried out isothermally at from 120 to 300° C. and with a feed rate of 0.5 to 10 mmol/min. of propyne and/or allene and from 0.5 to 20 mmol/min. of methanol. The reaction pressure was from 1.1 to 3.5 bar (absolute).

The total gas flow rate was as a rule from 4 to 60 l (S.T.P.)/h, said gas consisting of starting materials, inert gas and internal standard. The GHSV (gas hourly space velocity), which is defined as GHSV=Gasvolume[(S.T.P.)/h]/catalyst volume    (1)

was from 80 to 1200 h⁻¹. The LHSV (liquid hourly space velocity), which is defined as LHSV=liquid volume [l(s.t.p.)/h]/catalyst volume [l] (in this case the delivered volume of propyne and the methanol volume), was from 0.2 to 3 h⁻¹. The residence time, defined as the quotient of the catalyst volume [l] and the gas flow rate [l(s.t.p.)/s], was from 3 to 40 s.

After leaving the reactor, the reaction gases were passed via a heated transfer line (3) to an on-line gas chromatograph (B) and analyzed there every 2 hours. Thereafter, the gas stream was subjected to a partial condensation (C) and the part (6) not condensable at room temperature was analyzed by means of off-line GC at regular intervals (about 12 hours). The condensate (5) was likewise collected and analyzed by means of off-line GC.

Unless stated otherwise, the conversions and selectivities are based on the sum of propyne and allene.

b) Methods For Characterizing the Catalysts

Standard methods were used for characterizing the catalyst samples (fresh samples as well as samples removed from the reactor). The measured BET surface area and the hardness are stated in the respective example. Furthermore, the samples were thoroughly investigated by means of powder X-ray diffractometry (XRD) and transmission electron microscopy (TEM). The distribution of the zinc over the carrier was monitored by means of electron micrographs of sections and using a microprobe.

Selected samples were furthermore investigated by means of IR, ¹³C— and ²⁹Si-CP-MAS-NMR and EXAFS.

The enol ethers of the formula I which are obtainable according to the invention and the dialkoxy compounds of the formula II are useful intermediates for the preparation of active ingredients and fragrances. In particular, the enol ethers are desirable starting materials, for example for the preparation of γδ-unsaturated ketones as intermediates for the preparation of isophytol.

If it is intended in particular to obtain the enol ethers, the compounds of the formula II can be converted into the corresponding enol ethers of the formula I in a manner known per se by elimination of one mole of R¹OH. Numerous processes disclosed in DE-A-35 35 128, DE-A-37 22 891, DE-A-38 04 162, Chemical Abstracts, Vol. 94 (19); 156241 f and DE-A-19544450 exist for this purpose.

EXAMPLE 1 a) (Precatalyst: Content Calculated as Oxides: 20% of ZnO, 80% SiO₂)

The Zn/SiO₂ supported catalyst was prepared by impregnating X-ray amorphous SiO₂ moldings (beads of 3–6 mm diameter) having a BET surface area of 358 m²/g, a water absorptivity of 0.9 ml/g and a compressive strength of 43 N with ammoniacal zinc acetate solution.

For this purpose, 100 g of SiO₂ carrier (silica gel, from Solvay) were impregnated with 67.42 g of Zn (OAc)₂.2 H₂O (Merck) dissolved in 58 g of 25% strength NH₄OH solution at room temperature, and the precatalyst was then dried for 16 hours at 120° C. and then calcined for 4 hours at 250° C. under air.

The precatalyst had a BET surface area of 206 m²/g and a hardness of 64 N/molding. The acetate/zinc ratio was 0.56 mol/mol.

b) About 90 ml of the precatalyst were introduced into the apparatus described above. A propyne/allene mixture (about 55% strength by volume, 2.8 mmol/min) and methanol (2.1 mmol/min, total feed with inert substances, 7.3 mmol/min., methanol/propyne+allene ratio=0.75) were then metered in by means of HPLC pumps. The reaction temperature was 170° C. and the pressure was 1.2 bar (absolute) and the partial pressure of the starting materials was 0.8 bar. After formation of the catalyst was complete (after time-on stream of about 14 hours), the conversion was 67% (based on propyne and allene) or 90% (methanol). The main products formed (selectivity with respect to propyne+allene in brackets) were 2-methoxypropene (87%), 2,2-dimethoxypropane (4%), 1-methoxypropene (4%) and acetone (2%). The following values were determined for the completely formed catalyst after removal: BET 206 $m^2/g$, hardness 64N/molding.

EXAMPLE 2 a) (Precatalyst: Content Calculated as Oxides: 19.5% of ZnO, 0.5% of $Na_2O$, and 80% of $SiO_2$).

An impregnation solution consisting of 131.46 g Zn(OAc)$_2$.2H$_2$O (Merck) and 2.08 g of Na(OAc).3H$_2$O dissolved in a mixture of 160 g of distilled water and 120 g of 25% strength NH$_4$OH solution was divided into two parts of 195 ml each, and 200 g of $SiO_2$ carrier (Siliperl® AF125, from Engelhard) were impregnated at room temperature with the first part. The precatalyst was then dried for 16 hours at 120° C., impregnated with the second part at room temperature and were then dried for 16 hours at 120° C. and then calcined for 4 hours at 250° C. under air. The precatalyst had a BET surface area of 212 $m^2/g$ and a hardness of 61 N/molding. About 90 ml of the precatalyst were introduced into the apparatus described above and the propyne/allene mixture and methanol were then metered in by means of HPLC pumps. The reaction was continued at a first temperature setting of 170° C. until the active catalyst was completely formed and conversion and selectivity were constant. The temperature and the feeds were then changed. The results are summarized in Table 1. The pressure in all experiments was 1.2 bar (absolute).

Abbreviations: 2MP: 2-methoxypropene; 22DMP: 2,2-dimethoxypropane; 1MP: 1-methoxypropene (cis and trans); 11DMP: 1,1-dimethoxypropane.

of 25% strength NH$_4$OH solution at room temperature, and the precatalyst was then dried for 16 hours at 120° C. and then calcined for 4 hours at 250° C. under air. The precatalyst had a BET surface area of 246 $m^2/g$ and a hardness of 47 N/molding. About 90 ml of the precatalyst were introduced into the apparatus described above. A propyne/allene mixture (about 55% strength by volume, 2.6 mmol/min.) and methanol (2.1 mmol/min., total feed with inert substances: 7.0 mmol/min, methanol/(propyne+allene) ratio= 0.79) were then metered in by means of HPLC pumps. The reaction temperature was 170° C. and the pressure was 1.2 bar (absolute), and the partial pressure of the starting materials was 0.8 bar. After formation of the catalyst was complete (about 14 hours), the conversion was 69% (for propyne/allene) and 86% (for methanol). The products formed were (selectivities in brackets): 2-methoxypropene (86%); 2,2-dimethoxypropane (4%); cis- and trans-1-methoxypropene (4%); acetone (2%); 1,1-dimethoxypropane (1%). The following values were determined for the completely formed catalyst after removal: BET: 235 $m^2/g$, hardness 61 N/molding

EXAMPLE 4

(Precatalyst: Content Calculated as Oxides: 25% of ZnO, 75% of $SiO_2$)

The $SiO_2$ moldings were prepared as described in Example 1, in a one-stage ammoniacal impregnation. 100 g of $SiO_2$ carrier (silica gel) were impregnated with 89.89 g of Zn(OAc)$_2$.2 H$_2$O (Merck) dissolved in 55 g of 25% strength NH$_4$OH solution, and the precatalyst was then dried for 16 hours at 120° C. and then calcined for 4 hours at 250° C. under air.

The precatalyst had a BET surface area of 189 $m^2/g$ and a hardness of 56 N/molding. About 90 ml of the precatalyst were introduced into the apparatus described above. The propyne/allene mixture (about 55% strength by volume, 2.6 mmol/min.) and methanol (2.1 mmol/min., total feed with inert substances: 7.0 mmol/min, methanol/(propyne+allene) ratio)=0.79) were then metered in by means of HPLC pumps. The reaction temperature was 170° C. and the pressure was 1.2 bar (absolute), and the partial pressure for the starting materials was 0.8 bar. After formation of the catalyst was complete (about 14 hours), the conversion was 63% (for propyne/allene) and 85% (for methanol). The

TABLE 1

| | | Feed/mmol/min | | | Conversion | Selectivity/% | | | | |
|---|---|---|---|---|---|---|---|---|---|---|
| # | Temp. °C. | Propyne/ Allene | Methanol | Total | Propyne/ Allene | 2MP | 22DMP | Acetone | 1MP | 11DMP |
| 2.1 | 170 | 2.91 | 3.64 | 10.13 | 76% | 84 | 10 | 1 | 4 | 1 |
| 2.2 | 160 | 2.37 | 4.78 | 9.87 | 71% | 65 | 30 | 1 | 4 | 0 |
| 2.3 | 150 | 2.33 | 4.77 | 9.79 | 67% | 61 | 35 | 0 | 3 | 0 |
| 2.4 | 140 | 1.10 | 2.47 | 4.98 | 45% | 51 | 44 | 1 | 3 | 0 |
| 2.5 | 130 | 0.75 | 2.48 | 4.21 | 39% | 22 | 73 | 1 | 4 | 0 |

The following values were determined for the catalyst removed after the end of the experimental series: BET 213 $m^2/g$, hardness 45 N/molding.

EXAMPLE 3

(Precatalyst: Content Calculated as Oxides: 15% of ZnO and 85% of $SiO_2$)

The $SiO_2$ moldings were prepared as described in Example 1, in a one-stage ammoniacal impregnation: 100 g of $SiO_2$ carrier (silica gel, from Solvay) were impregnated with 47.59 g of Zn(OAc)$_2$.2 H$_2$O (Merck) dissolved in 54 g products formed were (selectivities in brackets): 2-methoxypropene (87%); 2,2-dimethoxypropane (4%); cis- and trans-1-methoxypropene (4%); acetone (2%); 1,1-dimethoxypropane (1%).

The following values were determined for the completely formed catalyst after removal: BET 222 $m^2/g$, hardness 73 N/molding.

EXAMPLE 5

If the procedure described in Example 1 or Example 2 is followed but the $SiO_2$ carrier used there is replaced by Siliperl® AF 125 (from Engelhard) or by the $SiO_2$ carrier D 11 - 10 or D 11 - 13 BASF Aktiengesellschaft) or an $SiO_2$ carrier whose surface has been rendered water repellent, comparable results are obtained.

EXAMPLE 6

For the preparation of the precatalyst, the procedure described in Example 1 was followed but the impregnation was carried out without the addition of any $NH_4OH$ After formation of the catalyst was complete (about 8 hours) the following selectivities were observed: 2-methoxypropene: 82%; acetone: 6%; 2,2-dimethoxypropane: 4%; cis and trans-1-methoxypropene: 4%; 1,1-dimethoxypropane: 1%. The propyne/allene conversion was 77%. The following values were determined for the completely formed catalyst after removal: BET 215 $m^2/g$, hardness 39 N/molding.

EXAMPLE 7

(Precatalyst: Content Calculated as Oxides: 7.5% of CdO, 7.5% of ZnO and 85% of $SiO_2$)

The $Cd/Zn/SiO_2$ supported catalyst was prepared by impregnating X-ray amorphous $SiO_2$ moldings (beads of 3–5 mm diameter) having a BET surface area of 413 $m^2/g$, a water absorptivity of 0.99 ml/g and a hardness of 29 N/molding with cadmium nitrate and zinc acetate solution. For this purpose, an impregnation solution consisting of 18.31 g of $Cd(OAc)_2.2\ H_2O$ (Merck) and 23.80 g of $Zn(OAc)_2.2\ H_2O$ (Merck) dissolved in 150 g of distilled water was divided into two portions of 95 ml and 85 ml, and 100 g of $SiO_2$ carrier (Siliperl® AF125, from Engelhard) were impregnated at room temperature with the first portion, and the precatalyst was then dried for 16 hours at 120° C., impregnated with the second portion at room temperature, then dried for 16 hours at 120° C. and finally calcined for 2 hours at 500° C. under air. The precatalyst had a BET surface area of 253 $m^2/g$ and a compressive strength of 40 N/molding. About 90 ml of the precatalyst were introduced into the apparatus described above, and the propyne/allene mixture (about 61% strength by volume, 3.2 mmol/min.) and methanol (2.0 mmol/min., total feed with inert substances: 7.5 mmol/min., methanol/(propyne+allene) ratio= 0.65) were then metered in by means of HPLC pumps. The reaction temperature was 170° C. and the pressure was 1.2 bar (absolute), and the partial pressure of the starting materials was 0.83 bar. After formation of the catalyst was complete (about 8 hours), the following selectivities were observed: 2-methoxypropene: 78%; 2,2-dimethoxypropane: 4%; acetone: 6%; cis- and trans-1-methoxypropene: 3%; 1,1-dimethoxypropane: 1%. The propyne/allene conversion was 61%. The following values were determined for the completely formed catalyst after removal: BET 241 $m^2/g$ and a hardness of 44 N/molding.

EXAMPLE 8 a) In situ formation of the catalyst at 200° C. (12.5% of ZnO)

500 g of $SiO_2$ powder (D11-10, BASF Aktiengesellschaft), prepared by precipitating silica having a BET surface area of 164 $m^2/g$, were first rendered water repellent by calcining at 900° C. for 2 hours. 100 g of the water repellent $SiO_2$ powder were kneaded with 3 g of potato starch, 2 g of a 25% strength ammonia solution and 140 g of water for 2 hours. The product was then extruded (pressure: 40 bar) and the extrudates were dried for 16 hours at 120° C. and calcined for 6 hours at 550° C. The carrier had a BET surface area of 127 $m^2/g$, water absorption of 1.0 ml/g and a hardness of <1 N/extrudate. 75 g of the $SiO_2$ carrier were impregnated with a solution of 28.90 g of $Zn(OAc)_2.2\ H_2O$ (Merck) in 74 ml of water in one step. Thereafter, the precatalyst was dried for 16 hours at 120° C. and calcined for 4 hours at 250° C. in the air. The precatalyst had a BET surface area of 74 $m^2/g$ and a hardness of 7 N/moldings. About 90 ml of the precatalyst were introduced into the apparatus described above, and the propyne/allene mixture (about 61% strength by volume, 3.1 mmol/min) and methanol (3.9 mmol/min, total feed with inert substances: 9.2 mmol/min; methanol/(propyne+allene) ratio=1.24) was then metered in by means of HPLC pumps. The reaction temperature was 200° C. and the pressure was 1.2 bar (absolute), and the partial pressure of the starting materials was 0.91 bar.

After an induction time of about 40 minutes, in which no reaction took place, the catalytic activity slowly began to develop. Directly after the onset of the catalytic activity, almost exclusively acetone and methyl acetate formed (the acetate originates from the decomposition of the zinc acetate). After about 80 minutes, the conversion of propyne/allene had reached as much as 35% (about half the final value) and the selectivity with respect to 2-methoxypropene was 53%. After about 150 minutes, the conversion of propyne/allene had reached as much as 67% (about 95% of the final value) and the selectivity with respect to 2-methoxypropene was 85%. After formation of the catalyst was complete (about 5 hours), the following selectivities were observed: 2-methoxypropene: 85%; 2,2-dimethoxypropane: 5%; acetone: 4%; cis- and trans-1-methoxypropene: 4%, 1,1-dimethoxypropane: 1%. The propyne/allene conversion was 71%. The following values were determined for the completely formed catalyst after removal: BET surface area 72 $m^2/g$; hardness 8 N/molding.

b) Preformation of the Catalyst at 200° C.

About 90 ml of the same precatalyst were introduced into the apparatus described above. Only methanol (3.9 mmol/min) was metered in during the first 4 hours. Only after this time was the metering of the propyne/allene mixture (about 61% strength by volume, 3.1 mmol/min., total feed with inert substances: 9.2 mmol/min., methanol/(propyne+allene) ratio=1.31) begun. From the beginning, the temperature in the reactor was kept at 200° C., the pressure at 1.2 bar (absolute) and the partial pressure of the starting materials at 0.91 bar. The catalyst then no longer had any induction period. About 10 minutes after the beginning of the propyne/allene metering, the conversion of propyne/allene was 53%. This value then remained substantially constant (56% conversion after a further 3 hours). The selectivity with respect to 2-methoxypropene also remained constant from the beginning. Three hours after the beginning of the propyne/allene metering, the following selectivities were observed: 2-methoxypropene: 80%; 2,2-dimethoxypropane: 8%; acetone: 5%; cis- and trans-1-methoxypropene: 4%, 1,1-dimethoxypropane: 1%. The following values were determined for the completely formed catalyst after removal: BET surface area 87 $m^2/g$, hardness 1 N/molding.

EXAMPLE 9 a) (Precatalyst: Content Calculated as Oxides: 20% of ZnO, 4% of $Cs_2O$ and 76% of $SiO_2$)

The $Zn/Cs/SiO_2$ supported catalyst was prepared by impregnating X-ray amorphous $SiO_2$ moldings (beads of 1.5–3.5 mm diameter) having a BET surface area of 300 $m^2/g$, a water absorptivity of 0.9 ml/g and a compressive strength of 35 N/molding with zinc acetate and cesium acetate solution. For this purpose, an impregnation solution consisting of 70.97 g of $Zn(OAc)_2.2\ H_2O$ (Merck) and 5.26 g of Cs(OAc) dissolved in 140 g of warm distilled water and 10 ml of acetic acid was divided into two portions of 90 ml and 80 ml, and 100 g of $SiO_2$ carrier (Siliperl® AF125, from Engelhard) were impregnated at room temperature with the first portion. The precatalyst was then dried for 16 hours at 120° C., impregnated with the second portion at room temperature, then dried for 16 h at 120° C. and finally calcined for 4 hours at 250° C. under air. The precatalyst had a BET surface area of 175 m²/g and a hardness of 47 N/molding. About 90 ml of the precatalyst were introduced into the apparatus described above, and the propyne/allene mixture (about 63% strength by volume, 3.3 mmol/min.) and methanol (3.9 mmol/min., total feed with inert substances:: 9.4 mmol/min., methanol/(propyne+allene) ratio=1.18) were then metered in by means of HPLC pumps. The reaction temperature was 200° C. and the pressure was 1.2 bar (absolute), and the partial pressure of the starting materials was 0.92 bar. After formation of the catalyst was complete (about 8 hours), the following selectivities were observed: 2-methoxypropene: 82%; 2,2-dimethoxypropane: 5%; acetone: 6%; cis and trans-1-methoxypropene: 5%; 1,1-dimethoxypropane: 1%. The propyne/allene conversion was 55%. The following values were determined for the completely formed catalyst after removal: BET 222 m²/g and a hardness of 47 N/molding.

b) (Precatalyst: content calculated as oxides: 20% of ZnO, 4% of $Li_2O$ and 76% of $SiO_2$)

The $Zn/Li/SiO_2$ supported catalyst was prepared by impregnating X-ray amorphous $SiO_2$ moldings (beads of 1.5–3.5 mm diameter) having a BET surface area of 300 m²/g, a water absorptivity of 0.9 ml/g and a hardness of 35 N/molding with zinc acetate and lithium acetate solution. For this purpose, an impregnation solution consisting of 70.97 g of $Zn(OAc)_2.2 H_2O$ (Merck) and 8.13 g of Li(OAc) dissolved in 140 g of warm distilled water and 10 ml of glacial acetic acid was divided into two portions of 90 ml and 80 ml, and 100 g of $SiO_2$ carrier (Siliperli® AF125, from Engelhard) were impregnated at room temperature with the first portion, and the precatalyst was then dried for 16 hours at 120° C., impregnated with the second portion at room temperature, then dried for 16 h at 120° C. and finally calcined for 4 hours at 250° C. under air. The precatalyst had a BET surface area of 210 m²/g and a hardness of 46 N/molding. About 90 ml of the precatalyst were introduced into the apparatus described above, and the propyne/allene mixture (about 63% strength by volume, 3.3 mmol/min.) and methanol (3.9 mmol/min., total feed with inert substances: 9.4 mmol/min., methanol/(propyne+allene) ratio=1.18) were then metered in by means of HPLC pumps. The reaction temperature was 200° C. and the pressure was 1.2 bar (absolute), and the partial pressure of the starting materials was 0.92 bar. After formation of the catalyst was complete (about 8 hours), the following selectivities were observed: 2-methoxypropene: 80%; 2,2-dimethoxypropane: 5%; acetone: 7%; cis and trans-1-methoxypropene: 5%; 1,1-dimethoxypropane: 1%. The propyne/allene conversion was 54%. The following values were determined for the completely formed catalyst after removal: BET 216 m²/g and a hardness of 48 N/molding c) (Precatalyst: content calculated as oxides: 17% of ZnO, 3% of $K_2O$, 79.7% of $SiO_2$ and about 0.3% of Pd)

The $Zn/K/SiO_2$ supported catalyst was prepared by impregnating X-ray amorphous $SiO_2$ moldings (beads of 1.5–3.5 mm diameter) having a BET surface area of 300 m²/g, a water absorptivity of 0.9 ml/g and a hardness of 35 N/molding with zinc acetate and potassium acetate solution. An impregnation solution consisting of 70.97 g of Zn(OAc)$_2$.2 H$_2$O (Merck) and 5.26 g of K(OAc) dissolved in 140 g of warm distilled water and 10 ml of acetic acid was divided into two portions of 90 ml and 80 ml, and 100 g of $SiO_2$ carrier (Siliperli® AF125, from Engelhard) were impregnated at room temperature with the first portion, and the precatalyst was then dried for 16 hours at 120° C., impregnated with the second portion at room temperature, then dried for 16 hours at 120° C., then impregnated with a 0.3% strength Pd-sol and again dried for 16 hours at 120° C. The precatalyst had a BET surface area of 169 m²/g and a hardness of 36 N/molding. About 90 ml of the precatalyst were introduced into the apparatus described above, and the propyne/allene mixture (about 63% strength by volume, 3.3 mmol/min.) and methanol (3.9 mmol/min., total feed with inert substances:: 9.4 mmol/min., methanol/(propyne+allene) ratio=1.18) were then metered in by means of HPLC pumps. The reaction temperature was 200° C. and the pressure was 1.2 bar (absolute), and the partial pressure of the starting materials was 0.92 bar. After formation of the catalyst was complete (about 8 hours), the following selectivities were observed: 2-methoxypropene: 85%; 2,2-dimethoxypropane: 4%; acetone: 3%; cis and trans-1-methoxypropene: 6%; 1,1-dimethoxypropane: 1%. The propyne/allene conversion was 74%. The following values were determined for the completely formed catalyst after removal: BET 184 m²/g and a hardness of 38 N/molding.

e) (Precatalyst: Content Calculated as Oxides: 7.5% of ZnO, 7.5% of CoO, 85% of $SiO_2$)

The $Zn/Co/SiO_2$ supported catalyst was prepared by impregnating X-ray amorphous $SiO_2$ moldings (beads of 3–5 mm diameter) having a BET surface area of 413 m²/g, a water absorptivity of 0.99 ml/g and a hardness of 39 N/molding with zinc acetate and cobalt(II) acetate solution. For this purpose, an impregnation solution consisting of 23.80 g of Zn(OAc)$_2$.2 H$_2$O (Merck) and 29.33 g of Co(OAc)$_2$.4 H$_2$O (Merck) dissolved in 150 g of warm distilled water was divided into two portions of 95 ml and 85 ml, and 100 g of $SiO_2$ carrier (Siliperl® AF125, from Engelhard) were impregnated at room temperature with the first portion. The precatalyst was then dried for 16 hours at 120° C., impregnated with the second portion at room temperature, and again dried for 16 hours at 120° C. The precatalyst had a BET surface area of 289 m²/g and a hardness of 39 N/molding.

About 90 ml of the precatalyst were introduced into the apparatus described above, and the propyne/allene mixture (about 60% strength by volume, 2.9 mmol/min.) and methanol (2.0 mmol/min., total feed with inert substances: 7.0 mmol/min., methanol/(propyne+allene) ratio=0.7) were then metered in by means of HPLC pumps. The reaction temperature was 170° C. and the pressure was 1.2 bar (absolute), and the partial pressure of the starting materials was 0.84 bar. After formation of the catalyst was complete (about 8 hours), the following selectivities were observed: 2-methoxypropene: 75%; 2,2-dimethoxypropane: 8%; acetone: 7%; cis and trans-1-methoxypropene: 3%; 1,1-dimethoxypropane: 1%. The propyne/allene conversion was 28%. The following values were determined for the completely formed catalyst after removal: BET 267 m²/g and a hardness of 49 N/molding.

EXAMPLE 10

($Al_2O_3$ carrier)

100.0 g of an $Al_2O_3$ carrier (3 mm extrudates, hardness 29.3 N/molding, water absorptivity 0.71 ml/g, BET surface area of 185 m²/g) were impregnated with 70.0 ml of tetramethoxysilane (Dynasil®, from Hüls). The tetramethoxysilane was then hydrolyzed by adding 15 ml of concentrated nitric acid. The $SiO_2/Al_2O_3$ carrier thus obtained was dried at 150° C. under $N_2$ for 15 hours. The carrier was then impregnated with a solution of 47.59 g of Zn(OAc)$_2$.2 H$_2$O (Merck) in 30 g of 25% strength aqueous ammonia (this corresponds to 15% of ZnO on $SiO_2/Al_{23}$). The extrudates obtained were then dried for 16 hours at 120° C. and calcined for 4 hours at 250° C. This precatalyst had a BET surface area of 166 m²/g and a hardness of 54 N/molding. About 90 ml of the precatalyst were introduced into the apparatus described above. Propyne/allene mixture (about 52% strength by volume, 2.9 mmol/min) and methanol (2.1 mmol/min, total feed with inert substances: 7.7 mmol/min, methanol/(propyne+allene) ratio=0.71) were then metered in by means of HPLC pumps. The reaction temperature was 170° C. and the pressure was 1.2 bar (absolute, partial pressure of the starting materials 0.78 bar). After an induction time of about 300 minutes, in which no reaction took place, the catalytic activity slowly developed. After formation of the catalyst was complete (about 20 hours), the following selectivities were observed: 2-methoxypropene: 69%; 2,2-dimethoxypropane: 8%; acetone: 12%; cis- and trans-1-methoxypropene: 8%, 1,1-dimethoxypropane: 1%. The propyne/allene conversion was 28%.

EXAMPLE 11
(Zinc Formate on Solvay Carrier)

The $Zn/SiO_2$ support catalyst was prepared by impregnating x-ray amorphous $SiO_2$ moldings (beads of 3–6 mm diameter) having a BET surface area of 358 $m^2/g$, a water absorptivity of 0.9 ml/g and a hardness of 43 N/molding with ammoniacal zinc formate solution, obtained by dissolving zinc formate dihydrate in $NH_4OH$-containing solution. 100 g of $SiO_2$ carrier (Siligel, from Solvay) were impregnated with 47.74 g of $Zn(HCOO)_2 \cdot H_2O$ dissolved in 120 g of 25% strength $NH_4OH$ solution at room temperature, and the precatalyst was then dried for 16 hours at 120° C. and then calcined at 250° C. for 4 hours under air. About 90 ml of the precatalyst were introduced into the apparatus described above. Propyne/allene mixture (about 46% strength by volume, 2.29 mmol/min) and methanol (2.11 mmol/min; total feed with inert substances: 7.20 mmol/min; methanol/(propyne+allene) ratio=0.92) were then metered in by means of HPLC pumps. The reaction temperature was 170° C. and the pressure was 1.20 bar (absolute, partial pressure of the starting materials 0.73 bar). After complete formation of the catalyst (after time-on stream of about 14 hours) the propyne/allene conversion was 29%. The following were formed as main products (selectivities relative to propyne+allene in brackets): 2-methoxypropene (77%), 2,2-dimethoxypropane (15%), 1-methoxypropene (4%) and acetone (3%).

EXAMPLE 12
(Zinc Acetylacetonate on Solvay Carrier)

The $Zn/SiO_2$ support catalyst was prepared by impregnating X-ray amorphous $SiO_2$ moldings (beads of 3–6 mm diameter) having a BET surface area of 358 $m^2/g$, a water absorptivity of 0.9 ml/g, and a hardness of 43 N/molding with methanolic zinc acetylacetonate solution, obtained by dissolving zinc acetylacetonate hydrate in methanol. 100 g of $SiO_2$ carrier (Siligel, from Solvay) were impregnated with 4×90 ml of a solution of 80.97 g of $Zn(acac)_2 \cdot xH_2O$ (Aldrich) in 360 ml of methanol at room temperature and dried for 16 hours at 120° C. after each impregnation step. Finally, calcining was carried out at 250° C. under air. About 90 ml of the precatalyst were introduced into the apparatus described above. Propyne/allene mixture (about 46% strength by volume, 2.45 mmol/min) and methanol (1.83 mmol/min; total feed with inert substances: 7.28 mmol/min; methanol/(propyne+allene) ratio=0.75) were then metered in by means of HPLC pumps. The reaction temperature was 170° C. and the pressure was 1.20 bar (absolute, partial pressure of the starting materials 0.71 bar). After formation of the catalyst was complete (after about 14 hours), the propyne/allene conversion was 65%. The following were formed as main products (selectivities relative to propyne+allene in brackets): 2-methoxypropene (84%), 2,2-dimethoxypropane (6%), 1-methoxypropene (4%) and acetone (2%).

We claim:
1. A process for the preparation of compounds of the formulae I and II

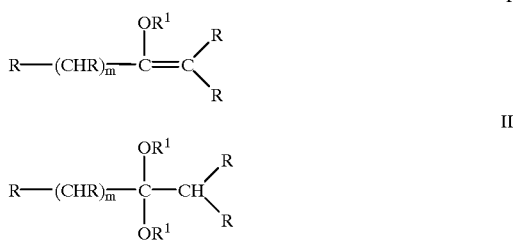

where $R^1$ is hydrogen or an aliphatic, cylcoaliphatic, araliphatic, aromatic or heterocyclic radical or an acyl radical, it being possible for these radicals to carry further substituents which do not react with acetylenes or allenes, and radicals R, independently of one another, are hydrogen or aliphatic, cycloaliphatic, araliphatic, aromatic or heterocyclic radicals which may be bonded to one another with formation of a ring, and m is 0 or 1, by addition reaction of a compound of the formula III $R^1OH$        III with an acetylene or allene of the formula IV or V

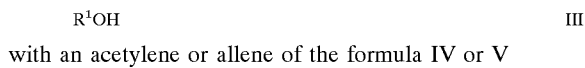

where $R^1$ and R have the abovementioned meanings, in the gas phase at elevated temperatures in the presence of a heterogeneous, silicate-containing catalyst, wherein the catalyst used contains, as an active component, an X-ray amorphous zinc silicate or cadmium silicate containing from 1 to 40% by weight, calculated as oxide, of zinc or cadmium, said catalyst being prepared by applying a zinc salt or cadmium salt of an organic acidic compound which is decomposable at below 400° C., to amorphous silica and forming the catalyst at from 50 to 500° C., in the presence of a hydroxyl-containing compound selected from the group consisting of water, alkanols of up to 10 carbon atoms, diols and polyols having 2 to 6 carbon atoms and 2 or 3 OH groups and carboxylic acids of 1 to 6 carbon atoms.

2. A process as claimed in claim 1, wherein said zinc salt is zinc acetate, zinc formate or zinc acetylacetonate is used.

3. A process as claimed in claim 1, wherein the catalyst used is one whose catalytically active component is furthermore doped with upto 80 mol per cent, based on zinc or cadmium, of further metals selected from the group (A) consisting of sodium, potassium, lithium, rubidium, cesium, beryllium, magnesium, calcium, strontium, barium, manganese, iron, cobalt, nickel and copper, and from the group (B) consisting of titanium, zirconium, hafnium, germanium, tin and lead.

4. A process as claimed in claim 1, wherein the catalyst used is one which was formed in the presence of the same alkanol as that to be reacted with the acetylene or allene.

5. A process as claimed in claim 1, wherein the catalyst used is one which is obtainable by impregnation of amorphous silica with a zinc salt in aqueous or aqueous ammoniacal solution and subsequent formation.

6. A process as claimed in claim 1, wherein the addition reaction of the hydroxyl-containing compound $R^1OH$ with the compounds of the formulae IV and V is carried out at from 100 to 350° C.

7. A process as claimed in claim 1, wherein 2-methoxypropene as the compound of formula I or 2,2-dimethoxypropane as the compound of formula II is prepared by addition reaction of methanol as the compound of formula III with methylacetylene as the compound of formula IV or allene as the compound of formula V at from 100 to 350° C.

8. A process for the preparation of an X-ray amorphous zinc silicate or cadmium silicate, wherein salts of zinc or of cadmium with an organic acidic compound which are decomposable at below 400° C. are applied to amorphous silica by dry blending or impregnation with a solution of the salts to form a precatalyst and the catalyst is formed at from 50 to 500° C.

9. A process as claimed in claim 8, wherein the precatalyst obtained by applying the zinc or cadmium salt to the amorphous silica is subjected, prior to formation of the catalyst at from 50 to 500° C., to a calcination at from 100 to 400° C., the temperature and the residence time during the calcination being chosen so that the precatalyst still contains at least 10 mol % of the original anion of the salts.

10. A process as claimed in claim 8, wherein an amorphous zinc silicate is obtained by impregnation of amorphous silica with a zinc acetate solution and followed by subsequent formation of the catalyst.

11. An X-ray amorphous zinc silicate or cadmium silicate catalyst as obtained by the process of claim 8.

12. An X-ray amorphous cadmium silicate obtained by the process of claim 8.

* * * * *